United States Patent [19]

Anthon

[11] Patent Number: 4,668,860
[45] Date of Patent: May 26, 1987

[54] SCATTERMETER USING POLARIZED LIGHT TO DISTINGUISH BETWEEN BULK AND SURFACE SCATTER

[75] Inventor: Erik W. Anthon, Santa Rosa, Calif.

[73] Assignee: Optical Coating Laboratory, Inc., Santa Rosa, Calif.

[21] Appl. No.: 785,905

[22] Filed: Oct. 9, 1985

[51] Int. Cl.$^4$ .............................................. G01J 4/00
[52] U.S. Cl. .................................... 250/225; 356/369
[58] Field of Search ................ 250/225; 356/367, 369, 356/446

[56] References Cited

U.S. PATENT DOCUMENTS 3,822,098  7/1974  Rudder et al. .................. 356/364 X
4,469,442  9/1984  Reich ............................. 250/225 X Primary Examiner—Eugene R. LaRoche
Assistant Examiner—David Mis
Attorney, Agent, or Firm—Flehr, Hohbach, Test, Albritton & Herbert

[57] ABSTRACT

Scattermeter for evaluating the surface quality of an optical element made from a material that has bulk scattering of light by measuring the light scattering from the surface while disregarding the bulk scatter, with the surface scatter being distinguished from the bulk scatter by their different polarization characteristics. The scattermeter is comprised of an illuminator optic providing an intense, substantially collimated light beam with a controlled variable state of polarization illuminating a defined area of the surface of said optical element. It is also comprised of a collector optic with a controlled field of view limited to an area substantially equal to the area illuminated by said illuminator optic, a polarization sensitive optical modulator, a photoelectric detector, a demodulating amplifier, and a readout device.

31 Claims, 8 Drawing Figures

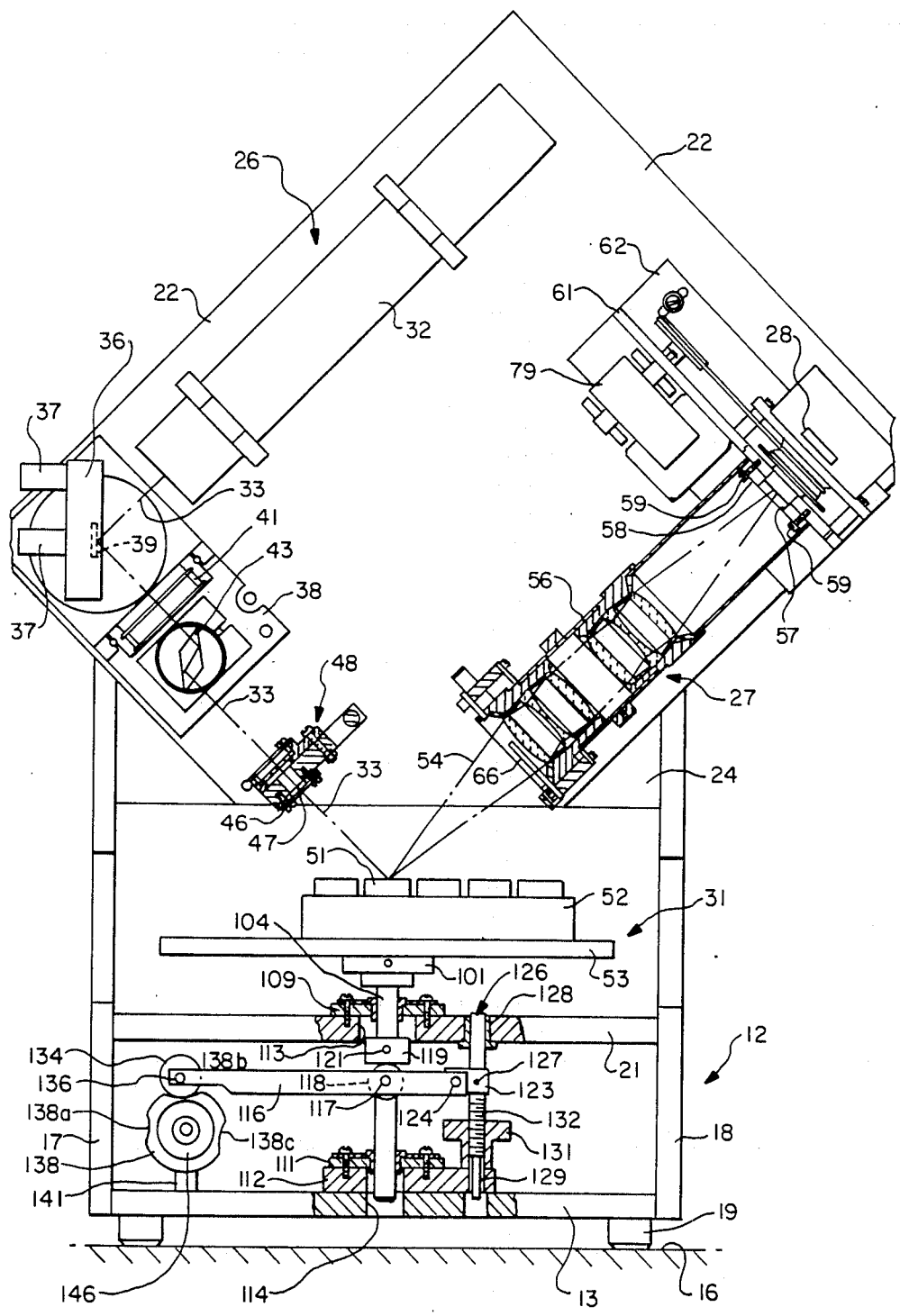
FIG.—1

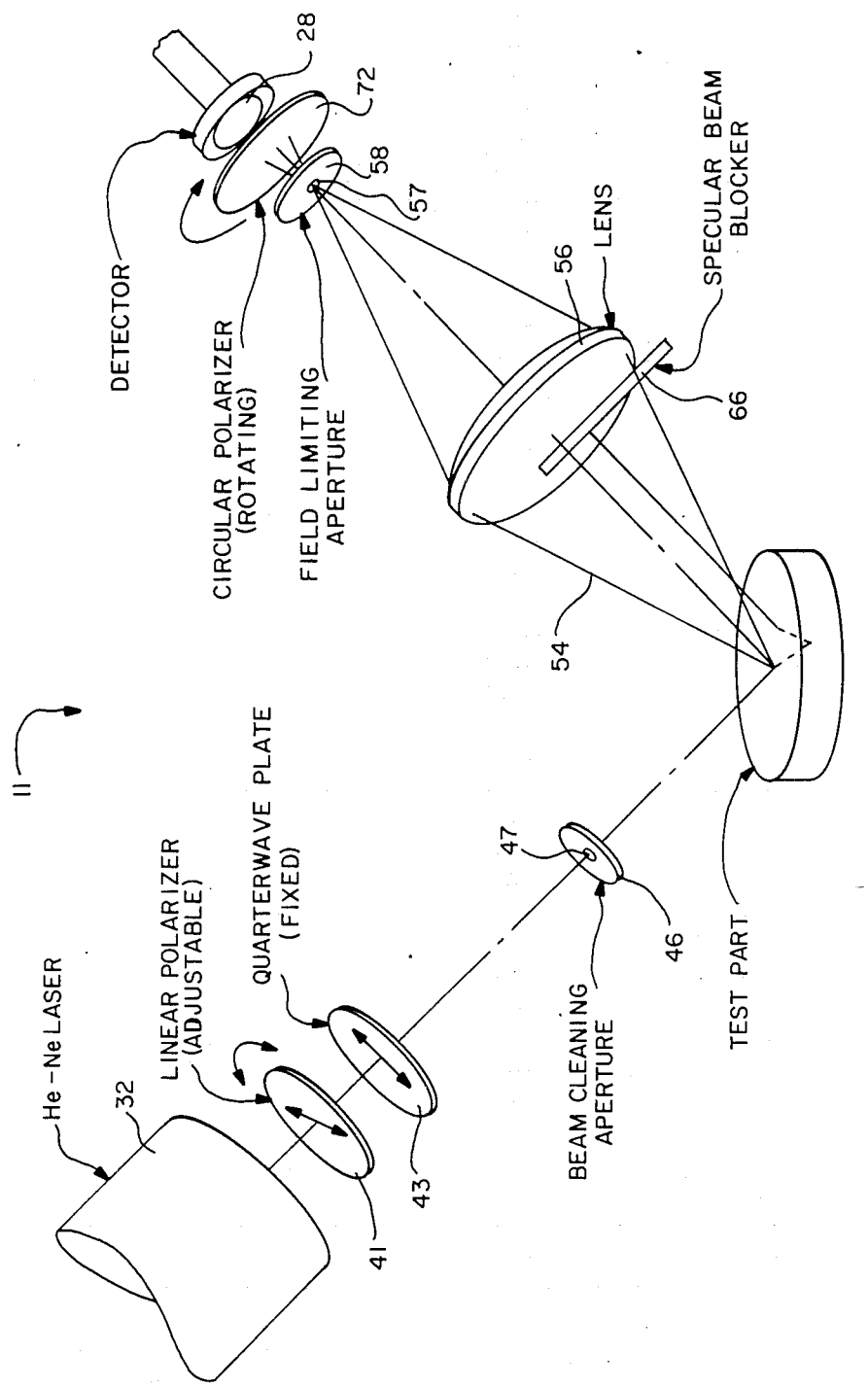
FIG.—2

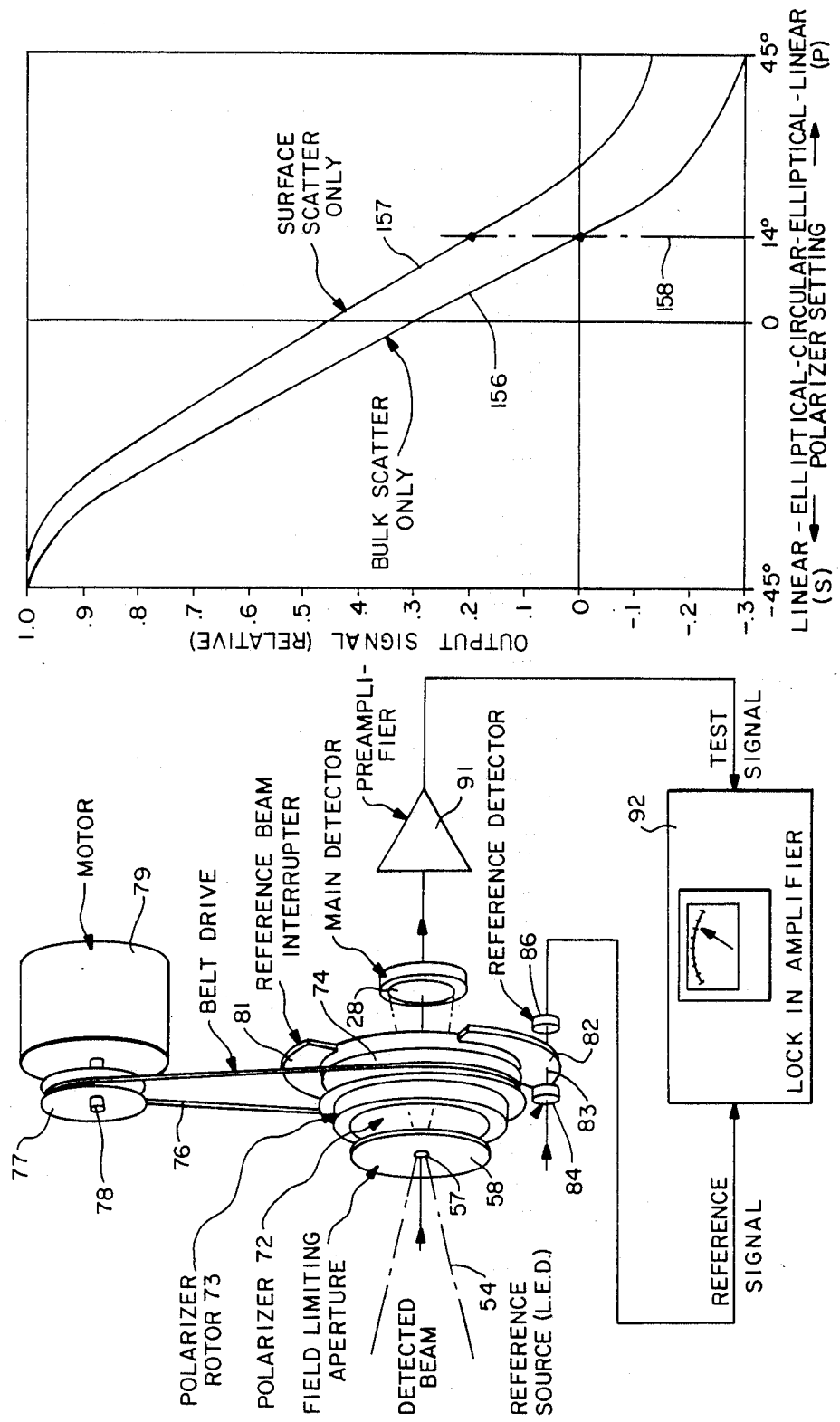

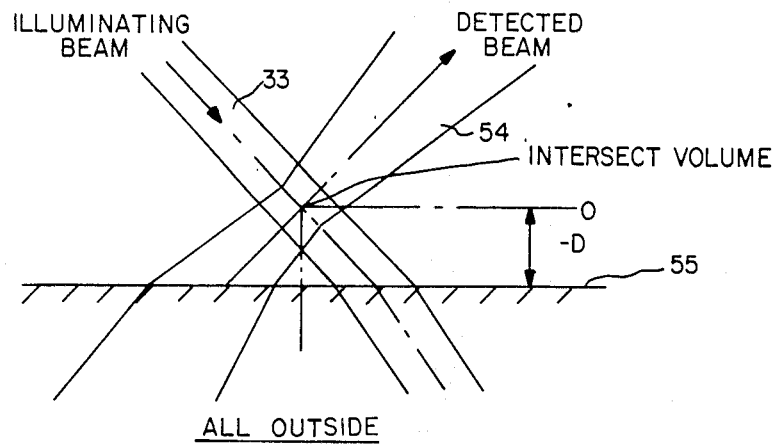
ALL OUTSIDE
FIG. — 4
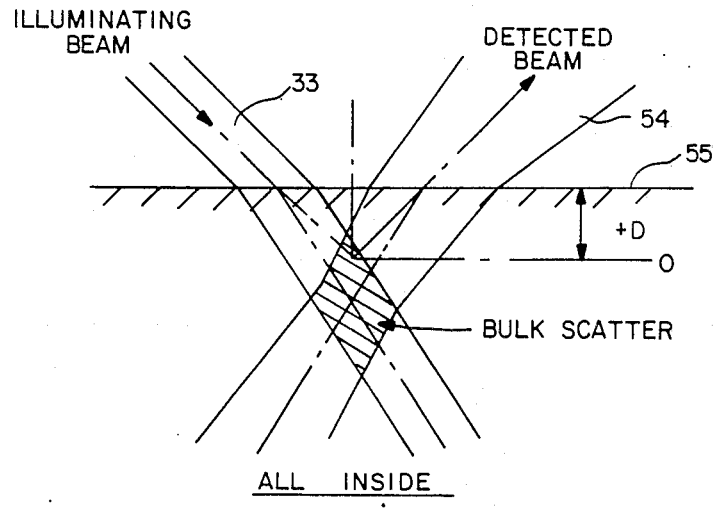
ALL INSIDE
FIG. — 5
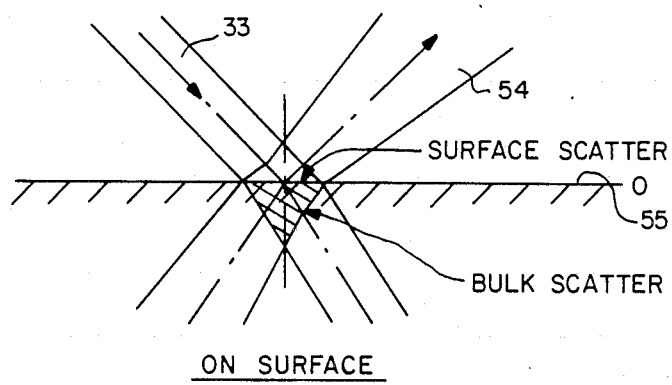
ON SURFACE
FIG. — 6 ized scattermeter and method for ascertaining surface scatter of milky materials in the presence of bulk scatter and a method for accomplishing the same.

Ceramic silica materials which are known under the trademarks of "Cervit", "Zerodur" and "Astrosital" have gained widespread acceptance for use in precision optical elements because these materials have an extremely low coefficient of thermal expansion, i.e., virtually zero. These materials, however, suffer a shortcoming in that they are not optically clear but have a milky appearance. In utilizing these materials for precision optical elements, highly polished surfaces are generally required. Surface quality is normally evaluated by making light scatter measurements. However, great difficulty is encountered in making light scatter measurements on ceramic silica materials because they appear milky and bulk scatter from the interior of the material greatly exceeds and drowns out any surface scatter from a well polished surface. Because of these problems, the evaluation of optical elements made from such materials is presently accomplished by metalization of the surface in question which requires termination of the polishing process. This is particularly undesirable in fabrication of precision optical elements and, in addition, is expensive. There is therefore a need for an apparatus and method which can evaluate the surface scatter of materials of this type during the polishing process so that the process can be continued until a desired surface quality is obtained.

In general, it is an object of the present invention to provide a polarizing scattermeter and method which can be used for evaluating the surface quality of precision optical elements formed from ceramic-silica materials.

Another object of the invention is to provide a scattermeter and method of the above character in which the surface quality is evaluated by making light scatter measurements.

Another object of the invention is to provide a scattermeter and method of the above character in which surface scatter is distinguished from bulk scatter by utilizing different degrees of polarization.

Another object of the invention is to provide a scattermeter and method of the above character which permits repeated polishing steps until the desired surface polish is attained.

Additional objects and features of the invention will appear from the following description in which the preferred embodiments are set forth in detail in conjunction with the accompanying drawings.

FIG. 1 is a front elevational view, partially in cross section, of a polarizing scattermeter incorporating the present invention.

FIG. 2 is a schematic illustration of the polarizing scattermeter shown in FIG. 1.

FIG. 3 is a schematic illustration showing a portion of the polarizing scattermeter shown in FIGS. 1 and 2 connected to electronic circuitry.

FIGS. 4, 5 and 6 are diagrams showing the method which is utilized in conjunction with the polarizing scattermeter shown in FIG. 1.

FIG. 7 is a graph showing what occurs to bulk scatter and to surface scatter during a rotation of the polarizer from −45° to +45°.

Figure 8:
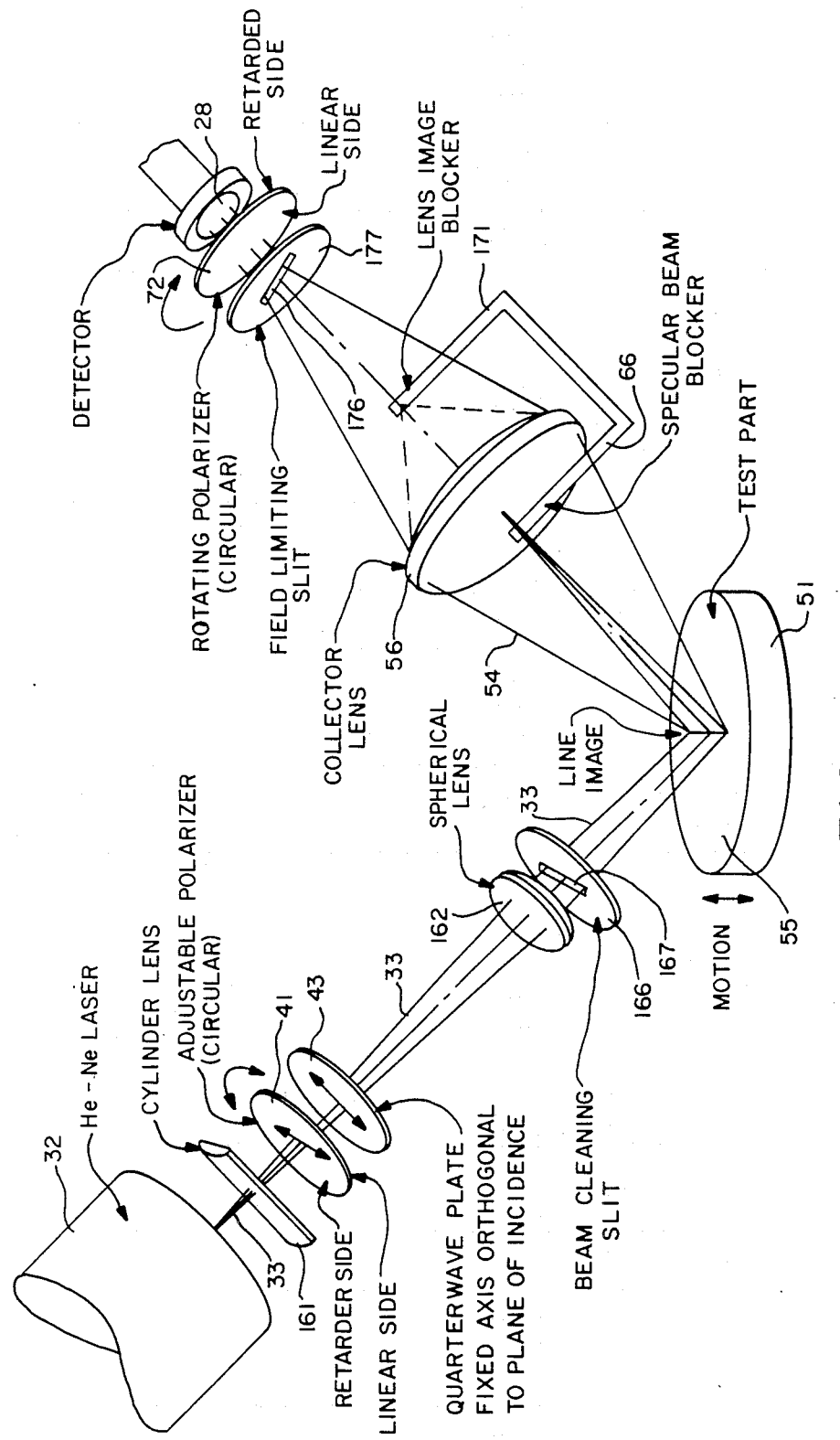
FIG. 8 is a schematic illustration showing another embodiment of a polarizing scattermeter incorporating the present invention.

The polarizing scattermeter 11 of the present invention consists of a stand or housing 12. The stand or housing 12 is provided with a base plate 13 which has feet 14 mounted on the lower surface thereof which are adapted to rest upon a support table or surface 16. A pair of spaced-apart side walls 17 and 18 are mounted upon the base plate 13 and extend vertically therefrom. A mounting plate 21 is mounted between the side walls 17 and 18. Another rectangular mounting plate 22 is provided which is disposed at an angle of 45° with respect to the vertical side walls 17 and 18. This mounting plate 22 is secured by suitable means to a cross member 24 which is secured to the side walls 17 and 18.

An illuminating optic 26, a collecting optic 27, and a detector 28 mounted upon the mounting plate 22. A platform 31 which can be raised and lowered as hereinafter described is provided below the illuminating optic 26 and the collecting optic 27.

The illuminating optic 26 consists of a helium-neon laser 32 operating at 632.8 nanometer wavelength which is used for illumination and provides a source of light. However, it should be appreciated that other lasers or other light sources can be utilzed if desired. The laser beam 33 strikes a mirror 34 which folds the beam through approximately 90°. The mirror 34 is disposed in a housing 36 which is provided with leveling screws 37 that make it possible to adjust the mirror 34 to aim the beam 33 which is reflected from a mirror 34. The housing 36 is carried by a mounting plate 38 which is secured to the larger mounting plate 22. The laser beam 33, after it is reflected by the mirror 34, passes through an adjustable linear polarizer 41 which is mounted on a mounting plate 38. The adjustable linear polarizer 41 can be a sheet polarizer or a crystal polarizer. The orientation of the polarizer 41 can be adjusted by rotation about an axis parallel to the axis of the laser beam 33.

After passing the linear polarizer 41, the laser beam 33 passes through the 90° (quarterwave) phase retarder 43. The phase sheet retarder 43 may be a crystal quarterwave plate or a stretched plastic retarder or alternatively, Fresnel's rhomb. The phase retarder must give an accurate 90° phase shift. It is mounted with its axis orthogonal to the axis of the optical system. The rhomb 43 is mounted on the plate 38 as shown in FIG. 1. The retarder or rhomb 43, in conjunction with the adjustable linear polarizer 41, determines the state of polarization of the laser beam 33. The polarization can be varied from linear p-polarization through elliptical to true circular polarization, through elliptical to linear s-polarization by a 90° adjustment of the polarizer 41. In other words, polarization of the outgoing beam from the retarder plate 43 can be varied from fully circular through elliptical with the axes orthogonal to the optical system, to a fully orthogonal, linearly polarized beam by adjusting the orientation of the linear polarizer. The beam 33, in normal operation, will be slightly elliptical with the p-component dominating.

Thereafter, the laser beam 33, after passing through the adjustable polarizer 41 passes through a beam-cleaning aperture plate 46 which is provided with a circular aperture 47. The beam-cleaning aperture plate 46 is carried by an assembly 48 which is mounted upon the mounting plate 22. The beam-cleaning aperture 47 serves to remove stray beams and scatter of the polarizer 41 before it strikes one of the test parts 51 at an angle of incidence of approximately 45°. By placing the small aperture 47 downstream from the origin of the beam 33, stray rays from the laser itself and from scatter from the polarizer 41 and the quaterwave retarder plate 43 are greatly reduced.

The test part or parts 51 are carried by a polishing block 52 which serves as a sample holder. The block 52 is placed on a rotatable platform 53. As hereinafter explained, the platform 53 positions the surface or surfaces of the test part or parts 51 such that the laser beam 33 strikes the surface of the test part 51 at an angle of incidence of 40° to 56° and preferably at an angle of approximately 45°. As hereinafter explained, the platform 53 can be raised and lowered to place the test point at the surface or below the surface of the test part. Alternatively, the platform 53 may be tilted to deviate the specularly-reflected beam. The platform also rotates about a vertical axis which preferably passes through the test point of the test part 51. This makes it possible to observe whether or not there are any grinding marks on the test pieces 51 which would tend to give higher scatter in one orientation than in another. The collecting optic 27 collects the reflected or detected beam 54 and consists of a lens assembly 56 which sees the test part 51 from an angle of incidence of 40° to 56°, and preferably at an angle of 45°. The lens assembly 56 can have a suitable f-number such as 3.5 and can collect a beam with an included angle of approximately 16°. However, a wider collection can be provided if desired by increasing from f:3.5 to f:1.7. The field of view of the lens assembly 56 is limited to an area equal approximately in size to the spot illuminated on the test part 51 by the laser beam 33 by a field stop in the form of a field-limiting aperture 57 provided in a plate 58 which is secured by screws 59 to a mounting plate 61. The mounting plate 61 is attached to a plate 62 which is secured to the plate 27. Typically, the illuminated spot provided by the laser beam would be approximately one milimeter in diameter. The lens assembly 56 has an imaging ratio of one-to-one. Thus the image of the spot would have a diameter of approximately one millimeter which is passed through aperture 57 which has a diameter of one millimeter. The detected beam 54 as shown on FIGS. 4, 5, and 6 is defined by the field of view of the lens as controlled by the field-limiting aperture 57 and the included angle of the beam collected by the lens as controlled by the f-number of the lens 56.

A blade 66 is provided in the front of the lens assembly 56 and extends inwardly from the outer perimeter of the lens assembly 56 into and past the central axis of the lens assembly 56. The blade 66 serves as a beam blocker and is of such a size so that it prevents the direct specularly-reflected laser beam from both the first and second surfaces of the test part from reaching the lens assembly 56 and only permits light scattered from the illuminated region of the test part 51 to pass through the lens assembly 56.

In other words, the collecting optic collects the energy around the specularly-reflected beam off the sample and images a test point onto a field stop. The specularlyreflected laser beam itself is blocked by a central obscuration in the collecting optic so that only the scattered rays go through the field stop.

Rather than using an imaging lens or a mirror system equipped with a central beam blocker as disclosed above, the collecting optic may be a Cassegrain-type mirror system with a natural central beam obscuration.

The detected beam 54 passing through the field-imagelimiting aperture 57 passes through a rotating polarizer 72. The rotating polarizer 72 can be positioned behind the collecting optic 27 as shown. Alternatively, it can be positioned in front of the collecting optic. The sheet polarizer 72, which is the rotating polarizer, is mounted in a rotor 73. The rotor 73 is driven at a high speed of approximately 2400 revolutions per minute and causes the sheet polarizer 72 to modulate the beam 54 according to its state of polarization. The rotor 73 is carried by a large pulley 74 which is driven by a belt 76. The belt 76 is driven by a pulley 77 mounted on an output shaft 78 of an electric motor 79. The pulley 74 is provided with two symmetrically placed arcuate lobes 81 and 82 which form a two-lobed beam interrupter that breaks the beam 83 between the reference source 84 (a light emitting diode) and the reference detector 86 twice with each revolution of the rotor 73. There is thus provided an optical switch which provides two pulses per revolution of the rotary polarizer 72.

The main detector 28 can be of a suitable type such as a silicon detector. The main detector 28 senses the detected laser beam 54 passing through the field stop or field limiting aperture 57.

The reference detector 86 provides a reference signal synchronous with the rotation of the polarizer 72; i.e., two cycles per revolution.

The output from the main detector 28 is supplied to a preamplifier 91. The output from the preamplifier 91 is a test signal which is supplied to a lock-in amplifier 92. The output from the reference detector 86 provides a reference signal which is also supplied to the lock-in amplifier 92. The lock-in amplifier 92 is of a conventional type and takes the signal from the main detector 28 and demodulates it with the signal from the reference detector 56. Only the linearily polarized component of the detected beam 54 will produce a modulated signal that can be demodulated by the lock-in amplifier 92. The demodulated output signal will be positive or negative depending on whether the s- or the p- component of linear polarization is dominant. The circular polarized component and the depolarized component of the detected beam 54 will not produce any modulated signal.

The two lobes 81 and 82 are required because if there is a peak in the polarization, the polarization will occur twice on each revolution.

The platform 53 is secured to the vertical shaft 104 with the hub 101. The shaft 104 is mounted in a pair of vertically spaced bearing assemblies 109 and 111 for vertical movement. The bearing assembly 109 is mounted on the plate 21 whereas the bearing assembly 111 is mounted upon a block 112 which is carried by the base plate 13. The shaft 104 extends through a hole 113 provided in the plate 21 and through holes 114 provided in the block 112 and the base plate 13.

Means is provided for adjusting the shaft 104 upwardly and downwardly and consists of an arm 116. The arm 116 has a pin 117 extending therethrough which carries a roller 118 which is adapted to engage a collar 119 provided on the shaft 104 and secured thereto by a set screw 121. The ends of the arms 116 on one side of the shaft 104 and pivotly connected to a block 123 by a pin 124. The block 123 is secured to a jack shaft 126 by a pin 127. The jack shaft 126 is mounted for vertical movement and has its upper extremity passing through a bearing 128 provided in the plate 21 and has its lower extremity passing through a bearing 129 provided in the block 112. A means is provided for adjusting the jack shaft 126 vertically and consists of a knurled knob 131 which is threadedly mounted on threads 132 provided on the jack shaft and engages the block 112 so that upon rotation of the knob 131, the jack shaft 126 can be raised and lowered.

The other end of the arm 116 has a cam follower 134 rotatably mounted on a pin 136. The arm 116 is secured to the pin 136. The cam follower 136 is adapted to engage a cam 138. The cam 138 is rotatably mounted upon a shaft 139 which extends into a block 141 secured to the base plate 13. A knurled knob 145 is also provided on the shaft 142 and is secured to the cam 138. Three indentations are provided on the cam 138 which have been identified as 138a, 138b, and 138c, respectively, in which the indentation 138a raises the platform 53 to its highest position, cam indentation 138b raises it to an intermediate position, and the indentation 138c lowers it to its lowermost position.

Operation and use of the polarizing scattermeter of the present invention in performing the method of the present invention may now be briefly described as follows. Let it be assumed that a large number of parts 51, for example as many as 20, are mounted on the block 52 by suitable means such as wax. The block 52 with the parts 51 thereon can then be positioned in the polishing machine and the top surfaces polished by a lap which moves over the top of the parts 51 using a slurry. To determine whether the desired polishing finish has been obtained, the block 52 with the parts still thereon are taken out of the polishing machine and the parts 51 are washed and cleaned very carefully. The surface of the parts 51 must be very clean because any dirt particles will scatter light and give an erroneous reading. The polishing block 52 is placed on the platform 53 with the exposed surfaces of the test part 51 facing upward. The part 51 to be tested is centered on the platform 53 and then the platform 53 is elevated to a suitable height in which the beam 33 impinges on the surface and is reflected into the collecting optic 27. The height of the platform 53 is adjusted by adjusting the knob 131 provided on the jack shaft 126.

The cam knob 146 is rotated so that the recess on indentation 138b underlies the cam follower 134. The platform 53 is raised or lowered. The jack shaft 126 with its associated knob 131 is provided for adjusting for variations in thicknesses of the polishing blocks 52. Thus the jack shaft 132 is adjusted so that the illuminating beam 33 intersects the detected beam 54 at the surface 55.

After the platform 53 has been adjusted to this position, the steps which are set forth in FIGS. 4, 5, and 6 are performed. To perform the step which is shown in FIG. 4, the knob 146 is grasped by the hand and the cam 138 is rotated until the recess 138c underlies the cam follower, so that the illuminating beam 33 and the detected beam 54 do not intersect within the part 51. It this position no surface or bulk scatter is collected. Any output signal observed for this position is caused either from stray light or electronic noise. Any signal, however, which is obtained on the lock-in amplifier when the test part is in the lowered position, is small and is nulled in the lock-in amplifier by the zero offset control. Only scatter generated within the intersect volume of the illuminating beam 33 and the detected beam 54 is collected.

After this step has been accomplished, the knob 146 is rotated until the recess 138a engages the cam follower 134 and raises the platform 53 to its uppermost position. In this position, the test part 51 is raised so that the intersection of the illuminating beam 33 and the detected beam 54 is within the test part 51 as shown in FIG. 5.

Only bulk scatter falls within the field of view of the detector in this position of the cam 138. The state of polarization of the detected beam will vary when the state of polarization of the illuminating beam is varied. Any signal observed on the lock-in amplifier 92 is optically nulled out by adjusting the setting of the adjustable polarizer 41 so that the collector beam from the bulk scatter contains no linear polarization component. This results in zero output from the lock-in amplifier and correct adjustment of the polarizer can readily be verified. The correct setting of the detected beam is found when the demodulated signal is zero. (The signal will be positive or negative depending on whether the s- or the p- component is dominate in the beam. The zero is not just a minimum, but a true null setting.

The effect of the bulk scattering is thus optically nulled out. It should be noted that it is qualitatively, not quantitatively, nulled. The bulk scatter will not produce an output signal regardless of how little or how much of it reaches the detector. When the adjustable linear polarizer is properly set, the polarizing scattermeter of the present invention is truly blind to bulk scatter and the next steps can be accomplished to measure surface scatter.

To accomplish this, the cam knob 146 is again rotated so that the recess on 138b underlies the cam follower 134 and the illuminating beam 33 intersects the detected beam 54 at the surface 55 as shown in FIG. 6. The surface scatter is now collected by the collecting optic 27. Bulk scatter is also collected in this position but will not contribute to any output signal because it has been optically nulled out as hereinbefore explained. The reading that appears on the lock-in amplifier 92 is solely attributable to the surface scatter from the surface 55 of the test part 51. Thus the reading given by the lock-in amplifier 92 is a direct measure of the quality of the surface finish of the test part. The readings which are obtained on the lock-in amplifier 92 for surface scatter are related to measurements of the specularly-reflected beam which can be collected by the detector 28 by temporarily removing the specular beam blocker 66.

Light reflected and light scattered off surfaces of optical elements at high angles of incidence (45° to 56°) tends to be highly linearly polarized. The present instrument is designed so that it is sensitive only to linearly polarized components of light and makes it possible to ensure that the inevitable bulk scatter will have a zero component of linear polarization.

From the foregoing it can be seen that the theory of operation of the instrument of the present invention is based upon the concept that light scattered off surfaces at high angles of incidence (45° to 56°) tends to be highly linearly polarized. The light scattered by bulk scattering tends to be less linearly polarized. The construction of the present instrument is such that it is sensitive only to the linearly polarized component by providing an illuminating optic which causes the inevitable bulk scatter to have a zero component of linear polarization. In other words, the operation of the instrument is based on the fact that there is a difference in the state of polarization of the light scattered from the surface and the light scattered from the inside (bulk) of the test part.

The signal detected and demodulated by the lock-in amplifier 92 is proportional to the content of the linearly polarized light in the detected beam. The signal will be zero if the detected beam is circularly polarized or randomly depolarized. Thus only linearly polarized components of the collected beam 54 will produce an output from the main detector 28. The state of polarization of the illuminating beam 33 and therefore of the collected scattered beam can be varied by the adjustable polarizer 41. The polarization of the illuminating beam 33 can be varied from linear s-polarization to elliptical, to circular, to elliptical to linear p-polarization through a 90° rotation of the adjustable polarizer 41. The major axis of the elliptical polarization will be orthogonal to the plane of incidence.

The degree of linear polarization in the collected beam and therefore the output signal level depends on the state of polarization of the illuminating laser beam 33. This is shown by the graph in FIG. 7. The signal level resulting from collecting either bulk scatter only or surface scatter only is shown by two curves, 156 and 157 respectively, which are plotted against the angular setting of the adjustable polarizer 41. The curve for the bulk scatter 156 only was measured by placing the test part 51 in the third position as shown in FIG. 7.

The surface scatter only was measured with the test part in the second position as shown in FIG. 4. The test part in this case was clear fused silica without bulk scatter. This is represented by the curve 157 in FIG. 7. FIG. 7 shows the results with the setting of the adjustable polarizer being −45° to +45°. As can be seen from FIG. 7, there is a point in the setting of the adjustable polarizer where the output signal from the bulk carrier will be zero while the output signal from the surface scatter is not zero. This is the working point which is sought and is represented by the vertical line 158 at +14°. The values for the signal levels are relative. The signal was set at 1.0 at the −45° setting of the adjustable polarizer 41.

It can be seen that there is a setting of the polarizer that gives zero output signal for bulk scatter while there is still a detectable output from the surface scatter. This condition exists for a polarizer setting of approximately +14° at 45° incidence. The effect of the bulk scatter is cancelled out, regardless of how little or how much bulk scatter there is under this condition and the surface scatter can be measured as if the bulk scatter did not exits.

The output signal that can be obtained from the surface scatter under the described condition is only a fraction of the maximum signal which is obtained at a polarizer setting of −45°. The fraction is 0.2 at 45° incidence.

Another embodiment of the polarizer scattermeter is shown in FIG. 8 and consists of the laser 32 which typically provides a beam which forms a round spot on the test object 51 which is converted to a sharp line image by a cylinder lens 161. This line image passes through an adjustable polarizer 41. A spherical lens 162 is introduced into the beam 33 remote from the adjustable linear polarizer 41 but to the rear of the beam-cleaning aperture plate 166 which is in the form of a slit 167. The cylinder 161 serves to spread out the beam 33 sideways whereas the spherical lens 162 serves to gather the beam up again. By using these lenses, the beam, at the time it impinges on the test surface, has a width of less than 1/10 of a millimeter and a length of approximately 3 millimeters. The introduction of the spherical lens 162 does create an additional problem in that it creates scatter which cannot be cleaned up by the beam-cleaning aperture 166. However, it has been found that the illuminated area of the spherical lens 162 forms an image behind the collecting lens 56 which is small enough so that it can be intercepted with a lens image blocker 171 and without blocking the total detected beam 54. The field limiting aperture for the detected beam 54 is made as small as possible and is in the form of a slit 176 provided in a plate 177.

The advantage of using a slit image rather than a circular or spot image is that the vertical motion of the platform 53 between the "in" and "out" positions as represented by FIGS. 4 and 5 is reduced by a factor of 10. In other words, with the dimensions given with respect to the embodiments shown in FIGS. 1 and 2 and the one shown in FIG. 10, the vertical motion D would be only 0.13 mm rather than 1.3 mm.

The lesser vertical motion makes the setting of the instrument to null out bulk scatter less sensitive. As is well known to those skilled in the art, when the bulk scatter has been nulled out in one position of the platform 53 carrying the part 51, it does not mean that it is perfectly nulled out in another position of the platform. However, if the motion required to move in and out of the beam is reduced, the variation is less and therefore the bulk scatter is effectively nulled out. The same is true with respect to the background stray light which is nulled out with the electrical nulling hereinbefore described.

The ratio of collected surface-to-bulk scatter is basically a surface-to-volume function. Intercept volume, and thereby the amount of bulk scatter, is greatly reduced by changing to a narrow line image.

It is advantageous to utilize the circular-type sheet polarizer rather than the simple linear polarizer sheet. The circular polarizer consists of a sheet of linear polarizer and a sheet of quarterwave retarder plate laminated together. The adjustable and the rotating polarizers are installed with their linear polarizer sides facing the test part 51 as shown in FIGS. 2 and 8.

The advantage of utilizing a circular polarizer for the adjustable polarizer is that it eliminates the variation in the intensity of the beam that would result from rotating a simple linear polarizer in front of the already linearly polarized laser beam. The advantage of using a circular polarizer for the rotating polarizer is that it eliminates the effect of any inherent sensitivity to linear polarization that the detector might have. Such sensitivity could cause severe false signals if a simple linear polarizer were used.

The level of sensitivity which can be measured by the instrument of the present invention can be illustrated by the fact that the intensity of the illuminating beam may be approximately 100,000,000 times that of the signal that is to be measured.

It is apparent from the foregoing that there has been provided a polarizing scattermeter and method which is capable of ascertaining surface scatter of milky materials in the presence of bulk scatter.

What is claimed is:

1. In a method for evaluating the quality of a surface of an optical element made from a material that creates bulk scattering of light impinging on the surface of the optical element, directing a substantially collimated light beam having a controlled variable state of polarization and measuring the surface scatter of light scattered from the surface of the optical element while disregarding the bulk scattering of light by distinguishing bulk scatter from the surface scatter by their different polarization characteristics.

2. A scattermeter for evaluating the surface quality of an optical element made from a material that has bulk scatter of light by measuring the intensity of surface scatter of light in the presence of the bulk scatter while disregarding the bulk scatter, said surface scatter and said bulk scatter being distinguished from each other by their different polarization characteristics, said scattermeter comprising an illuminator optic providing an intense, substantially collimated light beam with a controlled variable state of polarization illuminating a defined area of the surface of said optical element, a collector optic with a controlled field of view limited to an area substantially equal to the area illuminated by said illuminator optic, a polarization sensitive optical modulator, a photoelectric detector, a demodulating amplifier, and a readout device.

3. A scattermeter as in claim 2 wherein said collector optic consists of imaging means and a field-limiting aperture.

4. A scattermeter as in claim 3 wherein said iluminator optic consists of a continuous wave laser and an adjustable polarizing device combining linear polarizers and phase retarders.

5. A scattermeter as in claim 4 wherein the axis of said illuminating beam and the axis of said collector optic are in the same plane and both axes are at an angle of incidence ranging approximately from 45° to 57° relative to said surface of said optical element.

6. A scattermeter as in claim 5 together with a beam blocker for preventing specular reflection of said illuminating beam from said surface of said optical element from entering the collector optic.

7. A scattermeter as in claim 2 wherein the polarization of said illuminating beam is elliptical with axes orthogonal to the incidence plane defined by the illuminating and the collecting optics, together with means for adjusting the ellipticity of the polarization between the extremes of linear s-polarization and linear p-polarization through true circular polarization.

8. A scattermeter as in claim 7 wherein said means adjusting the ellipticity is comprised of a rotatable polarizer and a fixed quarterwave (90°) phase retarder with its axes orthogonal to the plane of incidence.

9. A scattermeter as in claim 7 wherein said means for adjusting the ellipticity of the polarization includes a sheet polarizer of the linear type.

10. A scattermeter as in claim 7 wherein said means for adjusting the ellipticity of the polarization includes a sheet polarizer of the circular type.

11. A scattermeter as in claim 2 wherein said polarization sensitive optical modulator is a rotating polarizer.

12. A scattermeter as in claim 11 wherein said rotating polarizer is a sheet polarizer of the linear type.

13. A scattermeter as in claim 11 wherein said rotating polarizer is a sheet polarizer of the circular type.

14. In a method for evaluation of the quality of a surface of an optical element made from a material that has bulk scattering, providing a substantially collimated illuminating beam having a controlled variable state of polarization impinging on said surface of said optical element whereby light is specularly reflected and scattered from the surface and bulk of said optical element, blocking the specularly reflected light, collecting the light scattered from the surface and bulk of the optical element, detecting only the linearly polarized components of the collected light and adjusting the state of polarization of said illuminating beam to such a degree of ellipticity that there is no linearly polarized component in the light collected from the scatter from the bulk of said optical element.

15. A method as in claim 14 together with the step of moving said optical element relative to said illuminating beam and collected beam such that only bulk scatter is collected, and adjusting the polarization of the illuminating beam until the detected signal becomes zero whereby the detecting of the collected light is effectively and qualitatively blind to bulk scatter.

16. In a polarizing scattermeter for evaluating the quality of a surface of an optical element that creates bulk scattering of light impinging upon the surface of the optical element, a source of substantially collimated light for providing an illuminating beam, adjustable means for polarizing the illuminating beam so that it has a controlled variable state of polarization, mounting means carrying the source of light and a defined area of the optical element for causing the illuminating beam to impinge upon the optical element to provide a reflected beam having therein light which is specularly reflected from and scattered from the surface and bulk of the optical element, means for adjusting the relative positions of the surface of the optical element and the beam to adjust where the beam impinges upon the optical element and detector means for detecting the reflected beam reflected from the optical element, whereby the bulk scattered light is nulled out optically and the surface scattered light is measured by the detector to provide a reading which indicates the quality of the surface finish of the optical element.

17. A scattermeter as in claim 16 together with a beam-cleaning aperture in the illuminating beam and a field limiting aperture in the reflected beam.

18. A scattermeter as in claim 17 wherein said beam-cleaning and said field limiting apertures are in the form of circular holes.

19. Apparatus as in claim 17 wherein said beam-cleaning and said field limiting apertures are in the form of slits.

20. A scattermeter as in claim 16 together with a rotating polarizer operating at a predetermined rate of speed, chopper means synchronized with said rotating polarizer for demodulating the signal provided by the detector.

21. A scattermeter as in claim 16 together with a collecting optic in the reflected beam having a lens and a specular beam blocker for blocking off a central portion of the beam before it passese through the lens.

22. A scattermeter as in claim 21 together with a collecting optic having a lens and a lens image blocker for blocking off a central portion of the reflected beam after it has passed through the lens.

23. A scattermeter as in claim 16 together with a turntable for supporting the optical element and means for moving the turntable into at least three different positions.

24. Apparatus as in claim 23 together with a cam having three recesses carried thereby, and roller means engaging the cam and the turntable.

25. Apparatus as in claim 24 together with a shaft, an arm connected to the cam follower, a jack screw, means pivotally conecting another part of the arm to the jack screw and means for vertically adjusting the jack screw.

26. In a polarizing scattermeter for evaluating the quality of a surface of an optical element that creates bulk scattering of light impinging upon the surface of the optical element, a turntable for supporting the optical element to be evaluated, means for raising and lowering the optical element between predetermined positions, a framework, means providing a substantially collimated source of light mounted on the framework, means for directing an illuminating beam from the source of light onto a defined area of the optical element to provide a reflected beam, a detector carried by the framework, collecting means carried by the framework for collecting light reflected from the optical element and directing it onto the detector, means connected to the detector for giving an output reading, an adjustable polarizer disposed in the illuminating beam, a polarizer disposed in the reflected beam, means for rotating the circular polarizer disposed in the reflected beam, chopper means operating in synchronism with the means for rotating the polarizer disposed in the reflected beam for chopping the output signal from the detector and means coupled to the chopper and to the detector for providing a reading of surface quality.

27. A scattermeter as in claim 26 together with a beam-cleaning aperture disposed in the illuminating beam and a field limiting aperture disposed in the reflected beam.

28. A scattermeter as in claim 27 wherein the beam-cleaning aperture and field limiting aperture have a circular configuration.

29. A scattermeter as in claim 27 wherein the beam-cleaning aperture and the field limiting aperture have an elongate configuration.

30. A scattermeter as in claim 27 wherein the adjustable polarizer is a linear polarizer.

31. A scattermeter as in claim 30 together with a quarterwave plate disposed in the illuminating beam.

* * * * *